United States Patent [19]

Kleinberg et al.

[11] 3,971,954
[45] July 27, 1976

[54] ULTRAVIOLET CAMERA SYSTEM FOR DENTAL PHOTOGRAPHY AND MOUTHPIECES THEREFOR

[75] Inventors: Israel Kleinberg, Smithtown, N.Y.; Alex Domokos, Winnipeg, Canada; Cosmo Castaldi, West Hartford, Conn.

[73] Assignee: Alphametrics Ltd., Winnipeg, Canada

[22] Filed: Nov. 11, 1974

[21] Appl. No.: 522,983

[30] Foreign Application Priority Data
Nov. 12, 1973  United Kingdom............... 52440/73

[52] U.S. Cl.................................... 250/475; 354/62
[51] Int. Cl.²......................................... G03B 41/16
[58] Field of Search ........... 250/475, 478, 479, 365; 32/71; 354/62

[56] References Cited
UNITED STATES PATENTS

| | | | |
|---|---|---|---|
| 2,072,390 | 3/1937 | van Hartingsvelt | 354/62 |
| 2,185,508 | 1/1940 | Kunze | 354/62 |
| 2,290,793 | 7/1942 | Alderman | 354/62 |
| 3,388,645 | 6/1968 | Sullivan | 354/62 |
| 3,479,937 | 11/1969 | Sullivan | 354/62 |
| 3,812,505 | 5/1974 | Elliot | 354/62 |

*Primary Examiner*—Alfred E. Smith
*Assistant Examiner*—D. C. Nelms
*Attorney, Agent, or Firm*—Stanley G. Ade

[57] ABSTRACT

A source of ultra violet light is directed onto the teeth of a patient via a mouthpiece which engages the gums above and below the tooth lines. A camera is attached and pictures may be taken of the teeth. By detecting differences in ultra violet absorption and reflection on the teeth, the detection of carious lesions may be undertaken in the relatively early stage of their development. Furthermore, deposits of dental plaque may be photographed readily and easily. The mouthpiece which may be disposable, is detachably securable to a base and is shaped at the mouth engaging end to engage the gums and hold the lips clear of the teeth during photography. It may be positioned in several locations relative to the mouth so that all of the teeth may be photographed and a mirror assembly may be attached so that the lingual and occlusal surfaces of the teeth may be photographed.

12 Claims, 8 Drawing Figures

3,971,954

ULTRAVIOLET CAMERA SYSTEM FOR DENTAL PHOTOGRAPHY AND MOUTHPIECES THEREFOR

This invention relates to new and useful improvements in ultraviolet camera systemms for dental photography and mouthpieces which facilitate the use of such cameras.

The detection of carious lesions by the use of ultraviolet photography is known, but these methods describe the use of the fluorescence or lack of fluorescence of the teeth due to the excitation wave lengths from ultraviolet light between 320 and 366 nanometers for the detection of such carious lesions.

These methods suffer from some disadvantages including difficulty in the detection of early carious lesions, it being understood that the earlier such lesions are detected, the easier they may be treated.

SUMMARY OF THE INVENTION

The present invention overcomes this disadvantage by enabling the best detection of carious lesions to be accomplished by detecting differences in ultraviolet absorption and reflection rather than ultraviolet excited fluorescence, particularly by using shorter ultraviolet wave lengths between 200 and 320 nanometers.

The spectral absorption curve of the material found in carious lesions led to the conclusion that carious lesions could be better detected by recording their relative absorption to the aforementioned shorter ultraviolet wave lengths.

The ultraviolet camera system described below enables photographs to be made of teeth by using the reflected radiation from an ultraviolet source emitting at a wave length between 200 and 320 nanometers, the wave length of 254 nanometers having been chosen in this particular instance.

The principal object and essence of the invention is therefore to provide a device of the character herewithin described in which the teeth are illuminated by ultraviolet light through a mouthpiece whereupon photographs are taken through the inside of the mouthpiece tube by means of an ultraviolet camera.

Another object of the invention is to provide a device of the character herewithin described which enables earlier detection of carious lesions to be made than heretofore to enable the dentist to distinguish between healthy and early diseased tissue during the cutting of such tissue in placing of a dental restoration. Conversely, to provide a device to assist in the repair of carious lesions, for example, by the use of components of a plastic nature or compounds designed to re-mineralize the lesions.

Another object of the invention is to provide a device of the character herewithin described which includes a novel mouthpiece attachable to a camera whereby the labial-buccal surfaces of all of the teeth and adjacent soft tissues may be photographed. In addition, a mirror may be provided so that the lingual and occlusal surfaces of the teeth and their adjacent soft tissues may also be photographed if the mouth has been partially opened.

Still another object of the invention is to provide a device of the character herewithin described which enables the necessary photographs of teeth to be taken rapidly and easily, with the least discomfort to the patient and without using a darkened room.

Another object of the invention is to permit photography of deposits of dental plaque on the teeth and surrounding soft tissues, plaque the bacterial and salivary deposits which are believed to be a cause of either dental caries or gum disease and is often responsible for tooth discoloration.

Another object of the invention is to permit detecting compositional differences in dental plaque for the purpose of determining those plaques which are pathogenic by using agents which combine with specific components of dental plaque and alter their ultraviolet characteristics.

Another object of the invention is to permit detection of caries around fillings which will assist in determining the need for their replacement.

Another object of the invention is to permit the recording and detecting of certain anomalies such as cracks and tooth mineralization lines (lines of retizus).

With the foregoing objects in view, and other such objects and advantages as will become apparent to those skilled in the art to which this invention relates as this specification proceeds, our invention consists essentially in the arrangement and construction of parts all as hereinafter more particualarly described, reference being had to the accompanying drawings in which:

BRIEF DESCRIPTION OF THE DRAWINGS

In the drawings like characters of reference indicate corresponding parts in the different figures.

DETAILED DESCRIPTION

Figure 2:
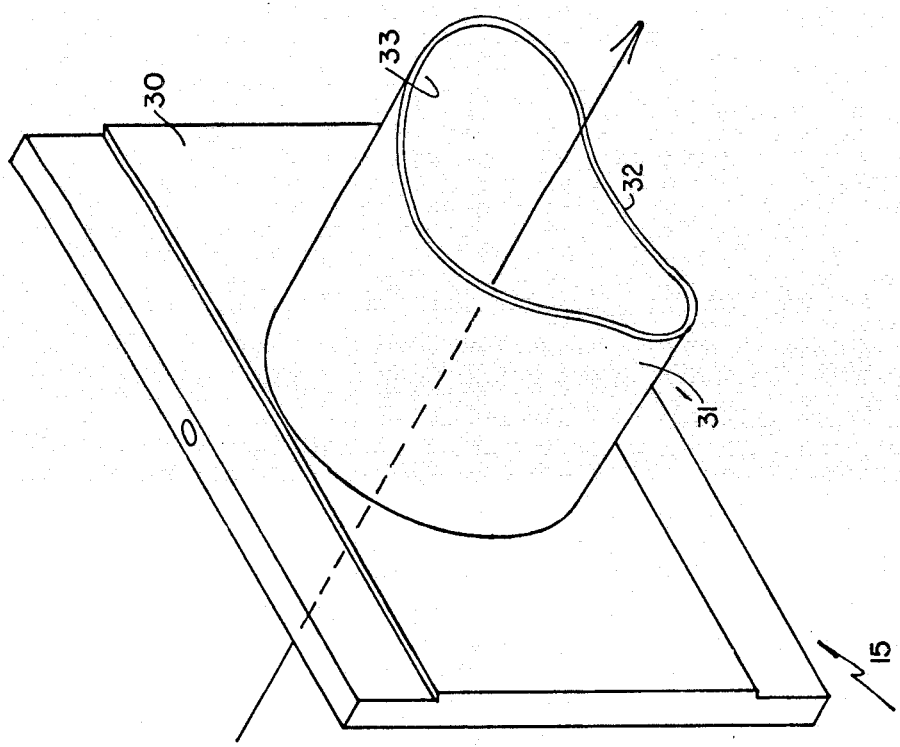
FIG. 2 is an enlarged isometric view of one embodiment of the mouthpiece.
Figure 1:
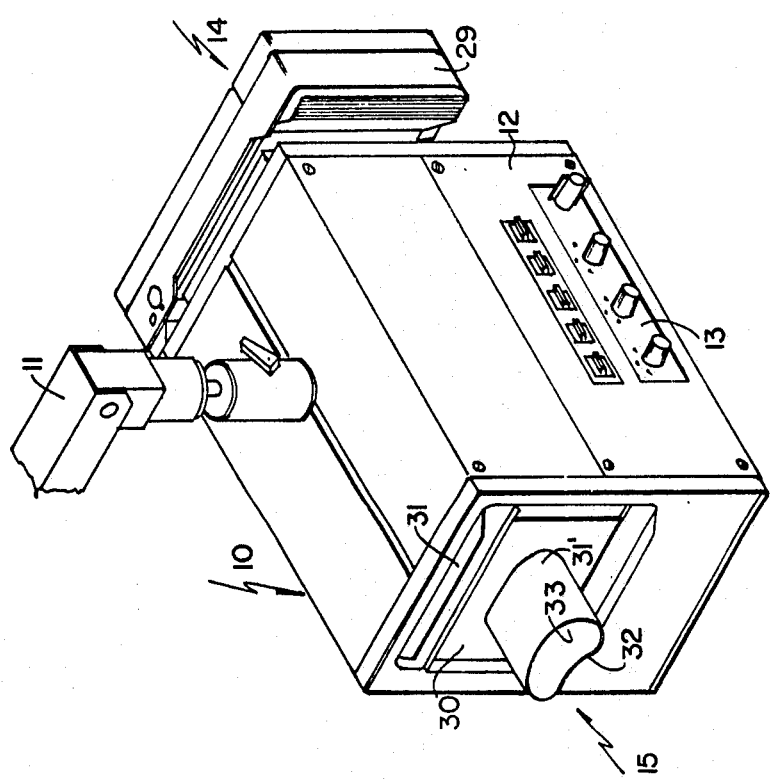
FIG. 1 is an isometric view of the ultraviolet camera with the mouthpiece attached thereto.

Proceeding therefore to describe the invention in detail, reference character 10 illustrates the overall camera structure which is preferably suspended by means of suspension 11 in a manner similar to the suspension used on dental X-ray machines.

The casing 12 includes the various components and a control panel 13 on one side thereof together with a camera back portion collectively designated 14 which is detachably secured to the rear of the casing 12.

A mouthpiece assembly collectively designated 15 is detachably secured to the front of the casing 12 and details of the construction of this mouthpiece will be described subsequently.

Figure 5:
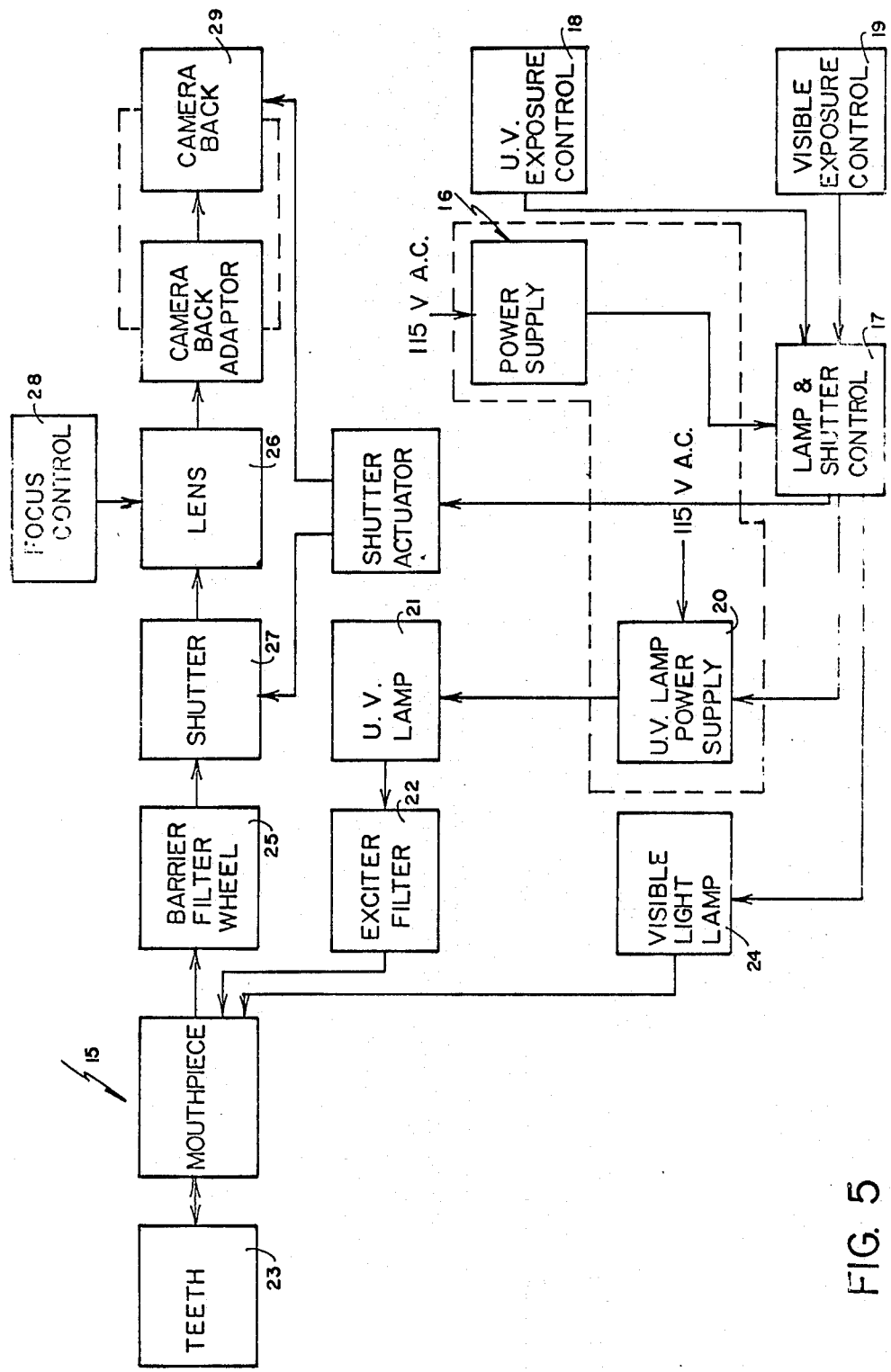
FIG. 5 is a schematic block diagram of the system per se.

FIG. 5 shows a schematic block diagram of the entire system, the majority of components being contained within the casing 12.

A power supply is indicated by reference character 16 which is connected to a lamp and shutter control 17 in turn controlled by ultraviolet exposure control 18 and visible exposure control 19.

The ultra violet lamp power supply is indicated at 20 which powers a low pressure mercury vapor lamp 21. Ultraviolet light from the lamp passes through an exciter filter 22 which restricts the ultraviolet radiation primarily to 254 nanometers, but does allow some additional radiation in the wave length region between 254 and 325 nanometers to pass.

This ultraviolet light passes to the mouthpiece 15 and thence to the teeth 23 as will hereinafter be described.

In order to facilitate the taking of the photographs to be made by visible light illumination, a visible light lamp 24 is provided which also reaches the teeth 23 through the mouthpiece 15.

The ultraviolet radiation passing through the mouthpiece 15 to the teeth 23 of the patient or subject, is reflected back through the mouthpiece to a barrier filter wheel 25 which contains several optical filters which can be controlled by a control knob on the instrument control panel 13 thereby allowing only a specific wave length range of radiation to pass through the filters to the lens 26 via the shutter 27. A focus control 28 is provided for the lens and the shutter and lens combination enables the operator to photograph either ultraviolet reflection, ultraviolet excited fluorescence or a combination of reflection and fluorescence.

The lens 26 in this embodiment uses only quartz and fluorite elements to achieve corrected transmission over a wave length range of 200 to 1000 nanometers. The ultraviolet radiation is focused by the lens onto the photographic film in the camera back 29. By the use of appropriate adaptors, which do not form part of this invention, either a 35 mm single lens reflex camera back, a polaroid camera back, a sheet film camera back, or a roll film camera back can readily be installed on the rear of the casing 12.

Electronically timed photographic exposures can be provided by the exposure control 18 or the visible exposure control 19.

Figure 4:
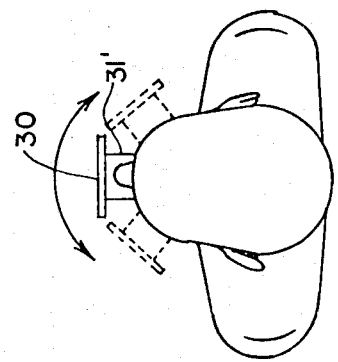
FIG. 4 is a top plan view of a patient showing the mouthpiece in the three positions necessary to photograph all of the teeth.
Figure 3:
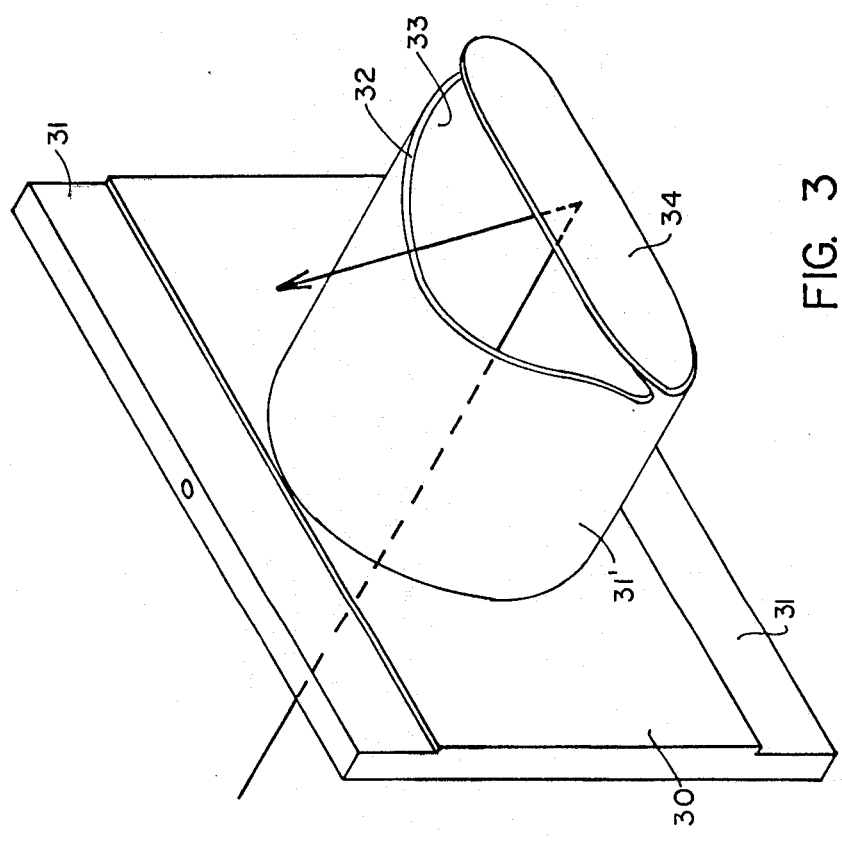
FIG. 3 is a view similar to FIG. 2, but showing an alternative embodiment.

FIGS. 2, 3 and 4 show details of the mouthpiece assembly collectively designated 15.

Dealing first with FIG. 2, an attaching base or panel 30 is provided which enables the mouthpiece assembly to be slid into position on the front of the casing 12 by means of flanges 31.

This base 30 is apertured and this aperture is surrounded by a mouthpiece tube 31' which is secured around the aperture and extends forwardly therefrom.

In one embodiment (FIG. 3), this tube is of a substantially oval cross sectional configuration and is provided with an outer end 32 which is shaped to approximately that of the front teeth of the subject. The shape ensures no extraneous light can enter the mouth, thus permitting the taking of photographs in a room that does not have to be darkened.

A plurality of different sized mouthpieces may be provided to accommodate different sized mouths.

The mouthpiece tube can be made of metal, plastic, paper and other suitable materials and the inside surface 33 of the tube may be finished to act as a reflector for the illuminating radiation.

In use, the mouthpiece is secured to the casing 12 and the mouthpiece is then inserted between the subject's lips with the contoured end 32 pushed against the gum surface above the upper teeth and below the lower teeth.

The teeth are illuminated by the ultraviolet or visible light source located in the casing 12, through the inside of the mouthpiece tube 31'. Photographs are taken through the inside of the mouthpiece tube via the barrier filter wheel, shutter and lens as hereinbefore described.

The mouthpiece can be positioned in the subject's mouth as shown in FIG. 4 and moved into the three positions illustrated so that the labial-buccal surfaces of all the teeth may be photographed in three separate photographs.

This enables rapid and reproducible photographs to be made of these two surfaces.

FIG. 3 shows an alternative embodiment in which the lower part of the front end 32 is provided with a mirror 34 which can be either plane or curved and situated at an angle so that the lingual and occlusal surfaces of the teeth can also be readily photographed if the mouth is partially opened.

Tests have indicated that the detection of early carious lesions can be made from the photographs taken with the present camera system using reflected radiation of approximately 254 nanometers. In addition, tests have shown that certain early carious lesions can be detected by the use of this system which cannot be detected by standard mirror-probe examination method.

Although FIG. 5 shows a schematic block diagram of a complete ultraviolet dental photography system, nevertheless it will of course be appreciated that it can be provided in a much more simple form, particularly from a commercial point of view.

Figure 6:
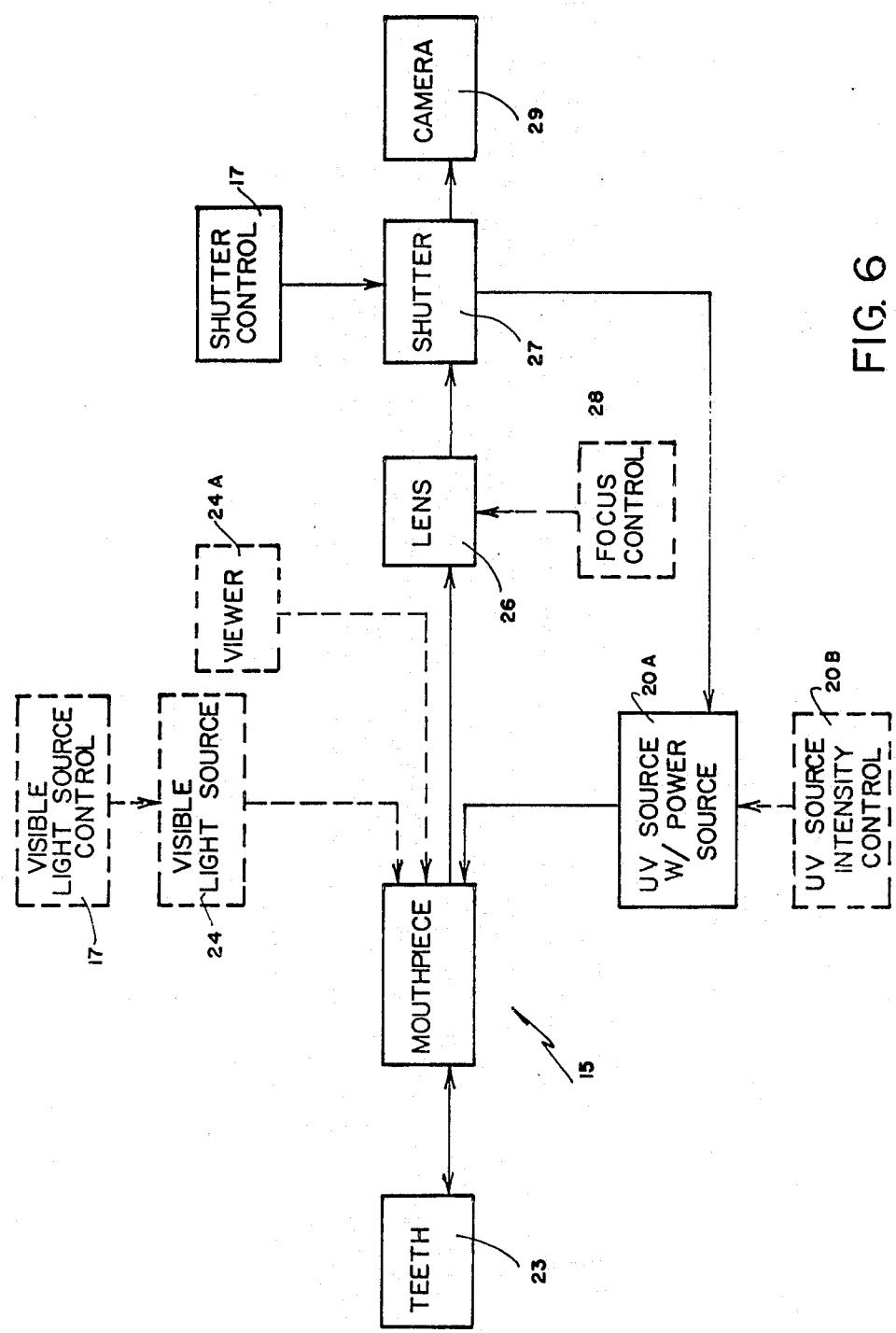
FIG. 6 is a schematic block diagram of a simplified system per se.

FIG. 6 shows an example of a simplified system which includes the mouthpiece 15, an ultraviolet source with power supply 20A, together with an ultraviolet source intensity control 20B which is optional.

The lens 26, shutter 27, shutter control 17 and camera back 29 are similar to those shown in FIG. 5 and optional focus control 28 may be provided for the lens if desired.

Also optional is the visible light source control 17 controlling a visible light source 24 together with a direct viewing means 24A.

Figure 8:
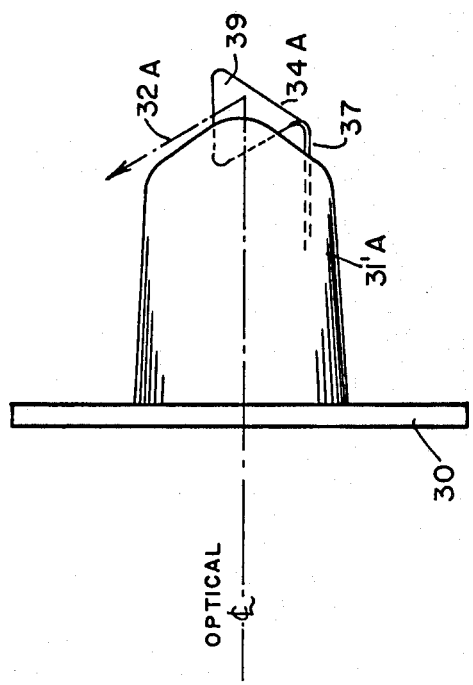
FIG. 8 is a side elevation of FIG. 7 in the assembled position.
Figure 7:
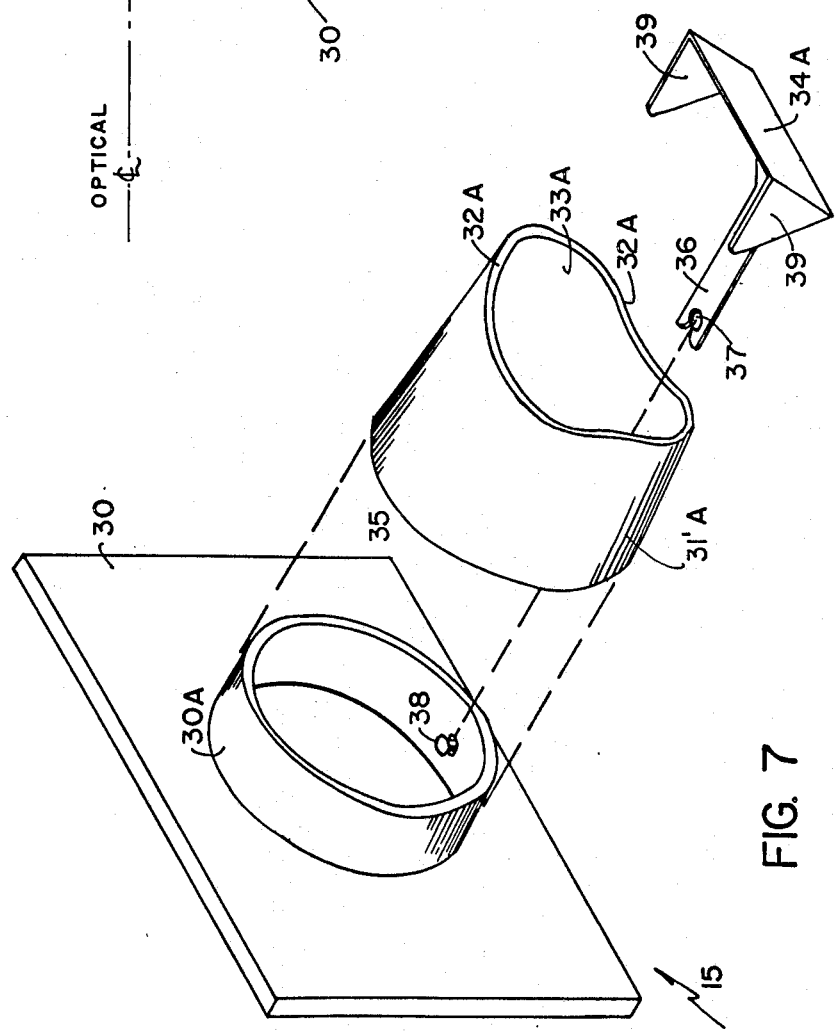
FIG. 7 is an exploded isometric view similar to FIG. 3 but showing a disposable and detachable mouthpiece and a detachable mirror.

FIGS. 7 and 8 show one embodiment of the mouthpiece and also of the detachable mirror unit and where similar items occur, similar numbers have been given, but with the suffix "A."

In the embodiment shown in FIGS. 7 and 8, a disposable mouthpiece 31A is provided.

These may be pre-packaged and sterilized and may be disposed of after one use.

A cylindrical collar 30A extends from the mouthpiece base 30 and the mouthpiece 31A slips over this collar and is held frictionally with the inner end 35 of the mouthpiece being of a similar cylindrical configuration.

The mirror assembly for unit 34A is provided with an attaching bracket 36 extending therefrom and having a slotted inner end 37. This bracket is engaged with a spring loaded member retaining clip or stud 38 extending upwardly from the collar 30A as clearly illustrated in FIG. 7.

The disposable mouthpiece is first slipped over the collar 30A and if the mirror is required, it is engaged with the stud 38 with the mirror wings 39 sliding just inside the sides of the mouthpiece 31A as shown in FIG. 8. Also in FIG. 8, the optical centre line is illustrated thus enabling photographs to be taken of the lingual and occlusal surfaces of the teeth, it being understood that the mouth has to be partially opened under these circumstances.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. A system for photographing the surfaces of the teeth and adjacent soft tissues, within the mouth of a patient, in conjunction with a camera and comprising in combination a hollow mouthpiece assembly detachably engageable within the said mouth of the patient, a source of ultraviolet light operatively connected to said mouthpiece whereby said ultraviolet light illuminates said teeth, and means to operatively connect said mouthpiece to the associated camera, the wave length of said ultraviolet light being between 200 and 380 nanometers.

2. The system according to claim 1 which includes a visible light source and viewing means also operatively connected to said mouthpiece.

3. The system according to claim 1 in which said mouthpiece includes an apertured base plate, a hollow mouthpiece tube surrounding said aperture and being secured to said base plate, the distal end of said mouthpiece being shaped to engage the upper and lower gums of the patient above the tooth line to prevent extraneous light from entering the mouth and to position the mouthpiece in the desired relationship relative to the associated camera.

4. The system according to claim 3 in which said mouthpiece tube is detachably secured to said base plate, said base plate including an extending flange having a configuration similar to the configuration of the attaching end of said mouthpiece tube, said mouthpiece tube frictionally and telescopically engaging over said extending flange.

5. The system according to claim 3 which includes a mirror assembly detachably securable to said mouthpiece for enabling photographs to be taken of the lingual and occlusal surfaces of the teeth and adjacent soft tissues.

6. The system according to claim 4 which includes a mirror assembly detachably securable to said mouthpiece for enabling photographs to be taken of the lingual and occlusal surfaces of the teeth and adjacent soft tissues.

7. The system according to claim 5 in which said mirror assembly includes a mirror, a bracket extending from the lower edge of said mirror and means on the distal end of said bracket detachably securing said mirror to said mouthpiece base, said means including a slotted portion formed on said distal end, and a spring loaded retainer clip on said mouthpiece base detachably engaged by said slotted portion to position said mirror at an angle and spaced from the distal end of said mouthpiece tube, said retaining clip extending from the wall bounding said aperture in said mouthpiece base, said bracket engaging through said mouthpiece tube.

8. The system according to claim 6 in which said mirror assembly includes a mirror, a bracket extending from the lower edge of said mirror and means on the distal end of said bracket detachably securing said mirror to said mouthpiece base, said means including a slotted portion formed on said distal end, and a spring loaded retainer clip on said mouthpiece base detachably engaged by said slotted portion to position said mirror at an angle and spaced from the distal end of said mouthpiece tube, said retaining clip extending from the wall bounding said aperture in said mouthpiece base, said bracket engaging through said mouthpiece tube.

9. A mouthpiece assembly for use within the mouth of a patient, a source of ultraviolet light comprising in combination an apertured base plate, a hollow opaque mouthpiece tube surrounding said aperture being secured to said base plate, the distal end of said mouthpiece tube being shaped to engage, simultaneously, the upper and lower gums of the patient above the tooth line to prevent extraneous light from entering the mouth and to position the mouthpiece in the desired relationship relative to the associated camera.

10. The mouthpiece assembly according to claim 9 in which said mouthpiece tube is detachably secured to said base plate, said base plate including an extending flange having a configuration similar to the configuration of the attaching end of said mouthpiece tube, said mouthpiece tube frictionally and telescopically engaging over said extending flange.

11. The mouthpiece assembly according to claim 9 which includes a mirror assembly detachably securable to said mouthpiece for enabling photographs to be taken of the lingual and occlusal surfaces of the teeth and adjacent soft tissues.

12. The mouthpiece according to claim 11 in which said mirror assembly includes a mirror, a bracket extending from the lower edge of said mirror and means on the distal end of said bracket detachably securing said mirror to said mouthpiece base, said means including a slotted portion formed on said distal end, and a spring loaded retainer clip on said mouthpiece base detachably engaged by said slotted portion to position said mirror at an angle and spaced from the distal end of said mouthpiece tube, said retaining clip extending from the wall bounding said aperture in said mouthpiece base, said bracket engaging through said mouthpiece tube.

* * * * *